(12) United States Patent
Jansma et al.

(10) Patent No.: US 10,005,751 B2
(45) Date of Patent: Jun. 26, 2018

(54) PROCESS FOR PRODUCING 4-AZIDOSULFONYLPHTHALIC ANHYDRIDE

(71) Applicant: Dow Global Technologies LLC, Midland, MI (US)

(72) Inventors: Matthew J. Jansma, Midland, MI (US); Michael F. Gullo, Midland, MI (US); John W. Hull, Jr., Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days. days.

(21) Appl. No.: 15/541,207

(22) PCT Filed: Dec. 28, 2015

(86) PCT No.: PCT/US2015/067597
§ 371 (c)(1),
(2) Date: Jun. 30, 2017

(87) PCT Pub. No.: WO2016/109389
PCT Pub. Date: Jul. 7, 2016

(65) Prior Publication Data
US 2017/0369464 A1    Dec. 28, 2017

Related U.S. Application Data

(60) Provisional application No. 62/097,786, filed on Dec. 30, 2014.

(51) Int. Cl.
*C07D 307/89* (2006.01)
(52) U.S. Cl.
CPC .................... *C07D 307/89* (2013.01)
(58) Field of Classification Search
CPC .................................................. C07D 307/89
(Continued)

(56) References Cited

U.S. PATENT DOCUMENTS 3,701,788 A    10/1972   Sayigh et al.
2016/0129166 A1   5/2016   Deniau et al.

FOREIGN PATENT DOCUMENTS

EP         0160218 A1    11/1985

OTHER PUBLICATIONS

Navarro, R., et al., Macromolecules, 2010, vol. 43, No. 5, 2377-2371.

(Continued)

*Primary Examiner* — Taylor V Oh
(74) *Attorney, Agent, or Firm* — Husch Blackwell LLP

(57) ABSTRACT

The present disclosure provides a process for the production of 4-azidosulfonylphthalic anhydride. In an embodiment, a process is provided and includes chlorinating 4-sulfophthalic acid trisodium salt (1), under solvent reaction conditions, to form a dissolved 4-chlorosulfonylphthalic anhydride (2) and an insoluble sodium chloride. The process includes first removing the insoluble sodium chloride from the dissolved 4-chlorosulfonylphthalic anhydride to form an isolated 4-chlorosulfonylphthalic anhydride. The process includes reacting, under solvent reaction conditions, the isolated 4-chlorosulfonylphthalic anhydride with sodium azide to form a dissolved 4-azidosulfonylphthalic anhydride and an insoluble sodium chloride. The process includes second removing the insoluble sodium chloride from the dissolved 4-azidosulfonylphthalic anhydride to form an isolated 4-azidosulfonylphthalic anhydride. The process includes retrieving a solid 4-azidosulfonylphthalic anhydride (3) from the isolated 4-azidosulfonylphthalic anhydride.

17 Claims, 5 Drawing Sheets

Synthetic Route for the Production of 4-Azidosulfonylphthalic Anhydride (3)

1
4-Sulfophthalic acid • 3Na
+ 15% 3-isomer

2
+ 15% 3-isomer
(isolated as solution in toluene)

3

(58) Field of Classification Search
USPC .......................................................... 549/250
See application file for complete search history.

(56) References Cited

OTHER PUBLICATIONS

Imai, Y., et al., Journal of Polymer Science: Polymer Chemistry Edition, vol. 11, 1973, 611-620.
Ulrich, H., et al., J. Org. Chem., vol. 40, No. 6, 1975, 802-804.

Synthetic Route for the Production of 4-Azidosulfonylphthalic Anhydride (3)

Block Flow Overview of the Process for the Production of 4-Azidosulfonylphthalic Anhydride (3) from 4-Sulfophthalic Acid, Trisodium Salt (1).

4-Azidosulfonylphthalic anhydride
($^{13}$C NMR, acetone-$d_6$, 100 MHz)

PROCESS FOR PRODUCING 4-AZIDOSULFONYLPHTHALIC ANHYDRIDE

BACKGROUND

Polyolefin grafted with azidosulfonylphthalic anhydride (ASPA) is known to be an effective composition for tie layer applications. Commercial supply of ASPA, however, is limited, unreliable, and difficult to obtain. The art therefore recognizes the need for additional sources and/or additional synthesis procedures for the reliable, consistent, efficient, and economical production of ASPA—and commercial scale production of ASPA in particular.

SUMMARY

The present disclosure provides unique synthetic pathways for the production of 4-azidosulfonylphthalic anhydride or ASPA. The processes disclosed herein are particularly advantageous for the commercial production of ASPA because of the efficiencies (i.e., efficiencies in terms of energy, cost, time, productivity, equipment, and/or readily available starting reagents) provided thereby. Provision of reliable ASPA advantageously simplifies production of tie layers made from polyolefin grafted with ASPA.

The present disclosure provides a process for the production of 4-azidosulfonylphthalic anhydride. In an embodiment, a process is provided and includes chlorinating 4-sulfophthalic acid trisodium salt (1), under solvent reaction conditions, to form a dissolved 4-chlorosulfonylphthalic anhydride (2) and an insoluble sodium chloride. The process includes first removing the insoluble sodium chloride from the dissolved 4-chlorosulfonylphthalic anhydride to form an isolated 4-chlorosulfonylphthalic anhydride. The process includes reacting, under solvent reaction conditions, the isolated 4-chlorosulfonylphthalic anhydride with sodium azide to form a dissolved 4-azidosulfonylphthalic anhydride and an insoluble sodium chloride. The process includes second removing the insoluble sodium chloride from the dissolved 4-azidosulfonylphthalic anhydride to form an isolated 4-azidosulfonylphthalic anhydride. The process includes retrieving a solid 4-azidosulfonylphthalic anhydride (3) from the isolated 4-azidosulfonylphthalic anhydride.

An advantage of the present disclosure is a process for large scale production, or commercial-scale production of ASPA.

An advantage of the present disclosure is a simple, time-effective, and/or cost-effective production process for ASPA.

DEFINITIONS

Figure 1:
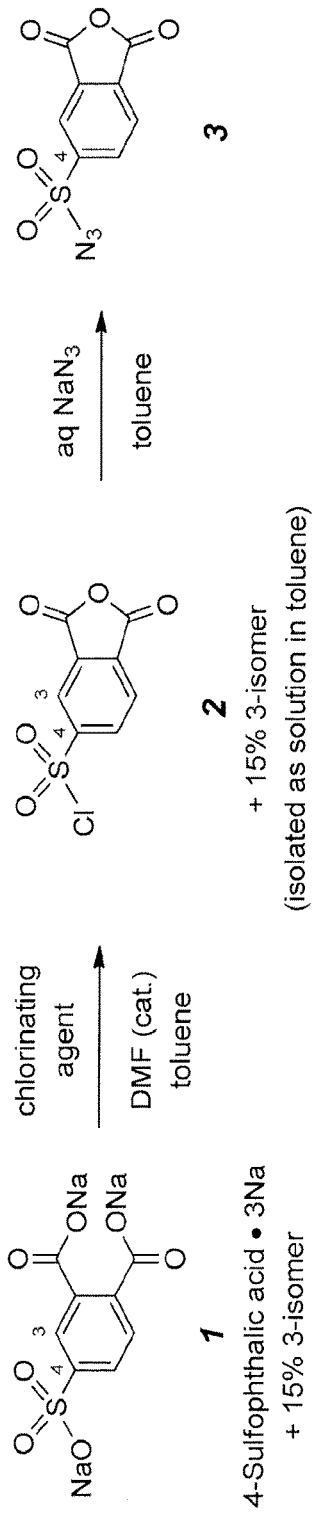
FIG. 1 is a reaction scheme for a process in accordance with an embodiment of the present disclosure.

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The numerical ranges disclosed herein include all values from, and including, the lower value and the upper value. For ranges containing explicit values (e.g., 1 or 2, or 3 to 5, or 6, or 7) any subrange between any two explicit values is included (e.g., 1 to 2; 2 to 6; 5 to 7; 3 to 7; 5 to 6; etc.).

The term "composition," as used herein, includes a mixture of materials which comprise the composition, as well as reaction products and decomposition products formed from the materials of the composition.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The term "ethylene-based polymer," as used herein, is a polymer that comprises a majority weight percent polymerized ethylene monomer (based on the total amount of polymerizable monomers), and optionally may comprise at least one polymerized comonomer.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers), terpolymers (which usually refers to polymers prepared from three different types of monomers or comonomers), tetrapolymers (which usually refers to polymers prepared from four different types of monomers or comonomers), and the like.

The term "polyolefin" is a polymer containing, in polymerized form, a majority weight percent of an olefin, for example ethylene or propylene, based on the total weight of the polymer. Nonlimiting examples of polyolefin include ethylene-based polymers and propylene-based polymers.

The term, "propylene-based polymer," as used herein, is a polymer that comprises a majority weight percent polymerized propylene monomer (based on the total amount of polymerizable monomers), and optionally may comprise at least one polymerized comonomer.

DETAILED DESCRIPTION

The present disclosure is directed to the production of 4-azidosulfonylphthalic anhydride (or "ASPA"). ASPA is found to be an effective graft component in olefin-based resins for tie layers. The processes disclosed herein advantageously provide economical (time, energy, productivity, and/or starting reagent economies), simplified, up-scalable synthesis pathways to ASPA with yields acceptable for commercial/industrial application thereof. Reliable production of ASPA correspondingly contributes to reliable and economical production of olefin-based polymer grafted with ASPA, a composition used as tie layer.

Figure 2:
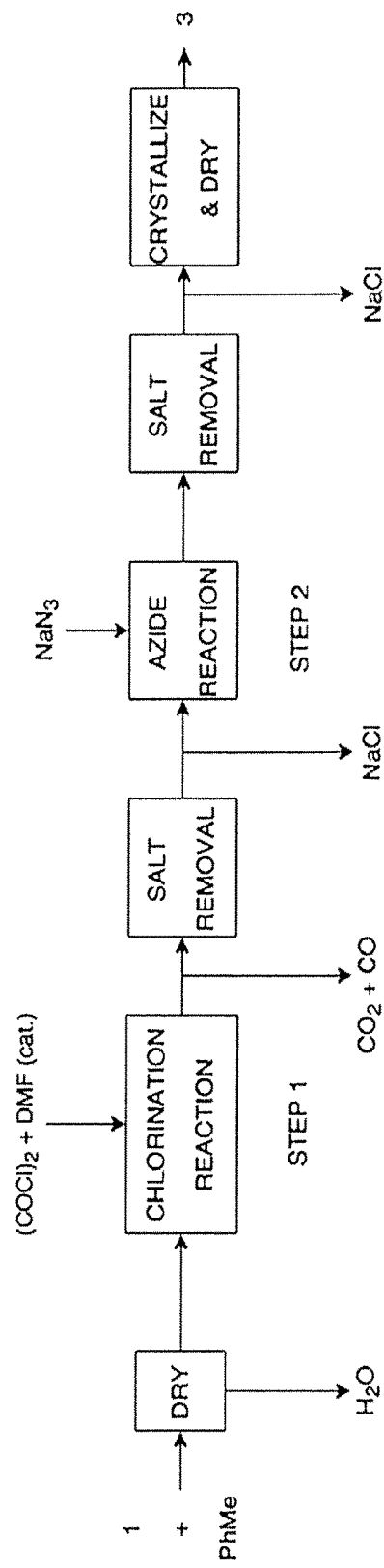
FIG. 2 is a block flowchart of a process in accordance with an embodiment of the present disclosure.

The present disclosure provides a process. In an embodiment, a process is provided and includes chlorinating 4-sulfophthalic acid trisodium salt (1), under solvent reaction conditions, to form a dissolved 4-chlorosulfonylphthalic anhydride (2) and an insoluble sodium chloride. As used herein, "solvent reaction conditions," are temperature, pressure, reactant concentrations, solvent selection, reactant mixing/addition parameters, and/or other conditions within a reaction vessel that promote reaction between the reagents and formation of the resultant product. The reaction is in the liquid phase. The insoluble sodium chloride is removed from the dissolved 4-chlorosulfonylphthalic anhydride to form an isolated 4-chlorosulfonylphthalic anhydride. The process includes reacting, under solvent reaction conditions, the dissolved 4-chlorosulfonylphthalic anhydride (2) with sodium azide to form a reaction product that is dissolved 4-azidosulfonylphthalic anhydride (3) and an insoluble sodium chloride. The process includes (second) removing the insoluble sodium chloride from the dissolved 4-azidosulfonylphthalic anhydride to form an isolated 4-azidosulfonylphthalic anhydride (3). The process includes retrieving solid 4-azidosulfonylphthalic anhydride (3) from the dissolved 4-azidosulfonylphthalic anhydride. Schematic representations of the process are shown in FIGS. 1 and 2.

The process utilizes 4-sulfophthalic acid trisodium salt (1) as a starting material. The structure of 4-sulfophthalic acid trisodium salt (1) is shown in FIG. 1. In an embodiment, prior to the chlorination, the process includes obtaining (or otherwise providing) a mixture of 4-sulfophthalic acid trisodium salt and trisodium salt isomer. The process includes removing residual water from the mixture of 4-sulfophthalic acid trisodium salt and trisodium salt isomer. The water is removed by subjecting the 4-sulfophthalic acid trisodium salt and trisodium salt isomer to a drying (or a pre-drying) step to form the 4-sulfophthalic acid trisodium salt (1). Alternatively, the 4-sulfophthalic acid trisodium salt and trisodium salt isomer is added to toluene and water solution and undergoes azeotropic co-distillation which removes the residual water to form the 4-sulfophthalic acid trisodium salt (1).

The process includes chlorinating 4-sulfophthalic acid trisodium salt (1), under solvent reaction conditions, to form a dissolved 4-chlorosulfonylphthalic anhydride (2) and an insoluble sodium chloride. The structure of 4-chlorosulfonylphthalic anhydride (2) is shown in FIG. 1. The term "chlorinating" or "chlorination" refers to the introduction of chloride into an organic compound. Chlorination occurs by way of reaction with a chlorinating agent. Nonlimiting examples of suitable chlorinating agents include oxalyl chloride [$(COCl)_2$], thionyl chloride ($SOCl_2$), phosphorus pentachloride ($PCl_5$), phosphorus trichloride ($PCl_3$), and phosphoryl chloride ($POCl_3$).

In an embodiment, chlorination is achieved by reacting the 4-sulfophthalic acid trisodium salt with oxalyl chloride, $(COCl)_2$, in toluene solvent and in the presence of catalytic N,N-dimethylformamide (DMF). The chlorination also forms sodium chloride as an insoluble precipitate in the toluene solvent. The 4-chlorosulfonylphthalic anhydride (2) remains soluble, or otherwise dissolved, in the toluene solvent.

In an embodiment, the chlorination of 4-sulfophthalic acid trisodium salt is conducted at a temperature from 20° C., or 50° C. to 60° C., or 80° C., or 100° C., or 110° C., with continuous addition of the chlorinating agent over a duration from 0.5 hours (h), or 1 h, or 1.5 h to 2 h, or 3 h. Once the addition of the chlorinating agent is complete, the reaction is optionally allowed to proceed for an additional 6 h, or 8 h, or 10, or 12 h, or 14 h to 16 h, or 18 h, or 20 h, or 22 h, or 24 h.

The process includes removing (or "first removing") the insoluble sodium chloride (precipitate) from the dissolved 4-chlorosulfonylphthalic anhydride to form an isolated 4-chlorosulfonylphthalic anhydride. The isolated 4-chlorosulfonylphthalic anhydride remains dissolved in the solvent, toluene.

In an embodiment, the first removing step includes filtering the sodium chloride from the dissolved 4-chlorosulfonylphthalic anhydride. The filtration procedure may include subsequent evaporation of a small amount of the toluene solvent in order to remove excess chlorinating agent from the isolated 4-chlorosulfonylphthalic anhydride.

In an embodiment, the first removing step includes filtering the insoluble sodium chloride from the dissolved 4-chlorosulfonylphthalic anhydride and subsequently washing the isolated 4-chlorosulfonylphthalic anhydride with a small portion of water to remove residual DMF. The washing procedure may include subsequent evaporation of a small amount of the toluene solvent in order to remove residual water from the isolated 4-chlorosulfonylphthalic anhydride.

In an embodiment, the first removing step includes adding water to the reaction mixture which includes toluene solvent, dissolved 4-chlorosulfonylphthalic anhydride, and insoluble sodium chloride. The water addition forms a liquid aqueous phase in the reaction mixture. The liquid aqueous phase digests, or otherwise dissolves, the insoluble sodium chloride. The toluene solvent forms a liquid nonaqueous phase in which the 4-chlorosulfonylphthalic anhydride remains dissolved.

The process includes separating the liquid aqueous phase from the liquid nonaqueous phase to remove the insoluble chloride from the dissolved 4-chlorosulfonylphthalic anhydride. In other words, the dissolved sodium chloride in the liquid aqueous phase is removed from the isolated 4-chlorosulfonylphthalic anhydride in the liquid nonaqueous phase by liquid (aqueous)-liquid (nonaqueous) phase separation. In an embodiment, the separation step includes a washing procedure whereby a subsequent evaporation of a small amount of the toluene solvent removes residual water from the isolated 4-chlorosulfonylphthalic anhydride.

The process includes reacting, under solvent reaction conditions, the isolated 4-chlorosulfonylphthalic anhydride (2) with sodium azide ($NaN_3$) to form 4-azidosulfonylphthalic anhydride (ASPA) (3). The structure of ASPA (3) is shown in FIG. 1. The solvent is toluene and the 4-azidosulfonylphthalic anhydride reaction product is dissolved (or otherwise is soluble) in the toluene. Insoluble sodium chloride as precipitate is also formed as a by-product.

In an embodiment, the reaction of 4-chlorosulfonylphthalic anhydride with sodium azide is conducted at a temperature from 0° C., or 15° C., to 20° C., or 30° C., or 40° C., or 50° C., with continuous addition of a solution of the sodium azide in water over a duration from 1 minute (min), or 3 min, or 5 min, to 7 min, or 9 min, or 10 min. Once the addition of the aqueous solution of $NaN_3$ is complete, the reaction is optionally allowed to proceed for an additional 1 h to 2 h.

In an embodiment, the sodium azide is added directly to the reaction vessel containing the isolated 4-chlorosulfonylphthalic anhydride dissolved in toluene. In other words, no intervening process steps occur (e.g., no purification, no isolation, no wash) between the removal of the insoluble sodium chloride from the reaction vessel and addition of the sodium azide to the reaction vessel. The toluene solvent used for the chlorination step is also used as the solvent for the sodium azide reaction and enables the use of the isolated 4-chlorosulfonylphthalic anhydride without further purification. In this way, the present process advantageously reduces process steps and reduces the amount of production equipment necessary to produce the ASPA end-product.

In an embodiment, the sodium azide is added as an aqueous sodium azide solution. The aqueous sodium azide solution contains from 5 wt %, or 10 wt %, or 20 wt %, or 25 wt % to 30 wt %, or 40 wt %, or 50 wt %, or 60 wt % sodium azide. Weight percent is based on total weight of the aqueous sodium azide solution. Applicant discovered that the addition of a solution of the sodium azide in water to the isolated 4-chlorosulfonylphthalic anhydride with toluene as reaction solvent advantageously avoids the need for a phase-transfer catalyst.

The process includes removing (or "second removing") the insoluble sodium chloride (precipitate) from the dissolved 4-azidosulfonylphthalic anhydride to form an isolated 4-azidosulfonylphthalic anhydride. The isolated 4-azidosulfonylphthalic anhydride remains dissolved in the toluene.

In an embodiment, the second removing step includes filtering the sodium chloride from the dissolved 4-azidosulfonylphthalic anhydride. The filtration procedure also includes the removal of any unreacted sodium azide.

The process includes retrieving the isolated 4-azidosulfonylphthalic anhydride as a solid. Typically, a small brine layer is present after the second removing step. The small brine layer is removed by phase separation. In an embodiment, the process includes recrystallizing the crude solid (3) to form a purified, solid 4-azidosulfonylphthalic anhydride (3). The isolated 4-azidosulfonylphthalic anhydride (3) dissolved in toluene is concentrated under vacuum to a crude solid. The crude solid is recrystallized from ethyl acetate/heptane to provide the purified and solid 4-azidosulfonylphthalic anhydride (3). In an embodiment, the purified and solid 4-azidosulfonylphthalic anhydride (3) has a purity from 92 wt %, or 93 wt %, or 94 wt %, or 95 wt %, or 96 wt %, or 97 wt % to 98 wt % or 99 wt %, or 99.9 wt %.

In an embodiment, the process is performed in a single reaction vessel. The chlorination, first removing, reacting, second removing, and the isolating steps are all performed in a single reaction vessel. The ability to perform the present process in a single reaction vessel advantageously improves production efficiencies by reducing the amount of equipment necessary to produce the 4-azidosulfonlyphthalic anhydride (3).

By way of example, and not limitation, examples of the present disclosure are provided.

EXAMPLES

1. Materials

The materials used in the examples are provided in Table 1 below.

TABLE 1

| Material | CAS Number | Source |
|---|---|---|
| 4-sulfophthalic acid, trisodium salt | 3325-08-4 | Sigma-Aldrich |
| N,N-Dimethylformamide (DMF) | 68-12-2 | Fisher or Sigma-Aldrich |
| Oxalyl chloride | 79-37-8 | Sigma-Aldrich |
| Sodium azide ($NaN_3$) | 26628-22-8 | Sigma-Aldrich |
| Toluene | 108-88-3 | Fisher |
| Ethyl acetate | 141-78-6 | Fisher |
| Heptane | 142-82-5 | Fisher |

2. Test Methods $^1$H- and $^{13}$C NMR spectra are recorded on a Bruker Ultrashield Plus 400 MHz spectrometer equipped with a B-ACS 60-sample changer and a 5 mm PABBO broadband probe with Z-gradients. $^1$HNMR spectroscopic data are referenced to the residual solvent peak when collected in acetone-$d_6$ (center line 2.05 ppm). When collected in deuterium oxide ($D_2O$), $^1$H NMR spectroscopic data are referenced to the trimethylsilyl proton resonance of 3-(trimethylsilyl)-1-propanesulfonic acid sodium salt (DSS sodium salt) [$(CH_3)_3SiCH_2$—$CH_2CH_2SO_3Na$, 0.00 ppm]. $^{13}$C NMR data are also referenced to the residual solvent peak when collected in acetone-$d_6$ (center line, 29.84 ppm). The following format is used to report $^1$H NMR resonances: chemical shift (δ, in ppm) [multiplicity, coupling constant(s) in Hz, integral value].

In-pot yield and final product purity are determined by $^1$H NMR assay with 1,4-bis(trimethylsilyl)-benzene (1,4-BTMSB) as an internal standard. Known quantities of the sample (e.g., crude reaction, final dry product) and 1,4-BTMSB are typically weighed into a 30-mL scintillation vial with the use of a precise analytical balance. The mixture is dissolved in acetone-$d_6$, passed through a 0.45 µm nylon syringe filter (if necessary to remove insoluble material), and the $^1$H NMR spectrum of the resulting mixture is collected (16 scans, 20 sec relaxation delay time). The wt % purity is then determined from the ratio of the average area/H integration for the resonances that correspond to the final product and the average area/H integration of the resonances for 1,4-bis(trimethyl silyl) benzene (1,4-BTMSB) [acetone-$d_6$: δ 0.25 (s, 18H) and 7.52 (s, 4H)]. The purity of 4-sulfophthalic acid, trisodium salt (1) is determined by $^1$H NMR assay with DSS sodium salt in $D_2O$. The wt % purity is determined in an identical manner as that described above by relative integration of the resonance corresponding to (1) against the resonances for DSS sodium salt {δ 0.00 [s, 9H, $(CH_3)_3SiCH_2CH_2CH_2SO_3Na$], 0.63 [dd, J=8.8, 8.8 Hz, 2H, $(CH_3)_3SiCH_2CH_2CH_2SO_3Na$], 1.76 [m, 2H, $(CH_3)_3SiCH_2CH_2CH_2SO_3Na$], and 2.91 [dd, J=7.6, 7.6 Hz, 2H, $(CH_3)_3SiCH_2CH_2CH_2SO_3Na$}.

3. Preparation of 4-Chlorosulfonylphthalic Anhydride (2) from 4-Sulfophthalic Acid, Trisodium Salt (1)

The reaction is performed in a 3-L jacketed glass reactor with a bottom drain that is equipped with an overhead mechanical stirrer, down-pumping two-tier 45° pitched 4-blade impeller (D=75 mm, 15 mm blade width, 75 mm tier separation), nitrogen inlet, thermowell, Dean-Stark trap, and a water condenser with a Teflon inner-tube which is vented to a scrubber containing a mechanically stirred solution of 10% aqueous sodium hydroxide. Temperature is controlled with a Neslab RTE 10 circulation bath using 80:20 Dow-Frost/water. The reactor is charged with 4-sulfophthalic acid, trisodium salt (1) (4:1 mixture with the 3-isomer) (350.0 g, 0.992 mol, 1.0 equiv, 88.5 wt % purity determined by $^1$H NMR assay with DSS sodium salt) and toluene (2600 mL) to produce an off-white slurry.

The mixture is then heated for the azeotropic drying step. Distillate is collected at an approximate internal temperature of 109° C. (heat transfer fluid bath temperature=115° C.). A total of 650 mL distillate is collected overhead. The resulting mixture is cooled to 50° C. and the Dean Stark trap is replaced with a water condenser/scrubber system. Anhydrous DMF (14.62 g, 0.198 mol, 20 mol %) is added and the reaction mixture is warmed to 50° C. Oxalyl chloride (322.6 g, 2.531 mol, 2.5 equiv) is loaded in portions to a 60-mL Teflon syringe and charged through a Teflon line to the reaction mixture over 3.5 hours via syringe pump. A slight exotherm of 1-2° C. is noted throughout the addition of the oxalyl chloride. The reaction mixture is stirred overnight at 50° C., and then cooled to room temperature. The mixture is removed through the bottom drain and the inorganic salts are collected by vacuum filtration through a coarse-porosity sintered glass frit funnel. The reactor is rinsed with fresh toluene which is passed through the inorganic salt wet cake. The toluene filtrate is partially concentrated by rotary evaporation and the fine white insolubles that are present are removed by filtration to provide 1423.1 g of toluene filtrate. A sample of the toluene filtrate (1.0164 g) is removed, evaporated to dryness, and combined with 1,4-BTMSB (37.0 mg, 0.1658 mmol). The resulting mixture is dissolved in acetone-d$_6$ (~4 mL). Analysis of this sample by $^1$H NMR indicates that the concentration of (2) (4:1 mixture with the 3-isomer) is 11.0 wt %, which corresponds to an in-pot yield of 64% (0.635 mol).

Figure 3:
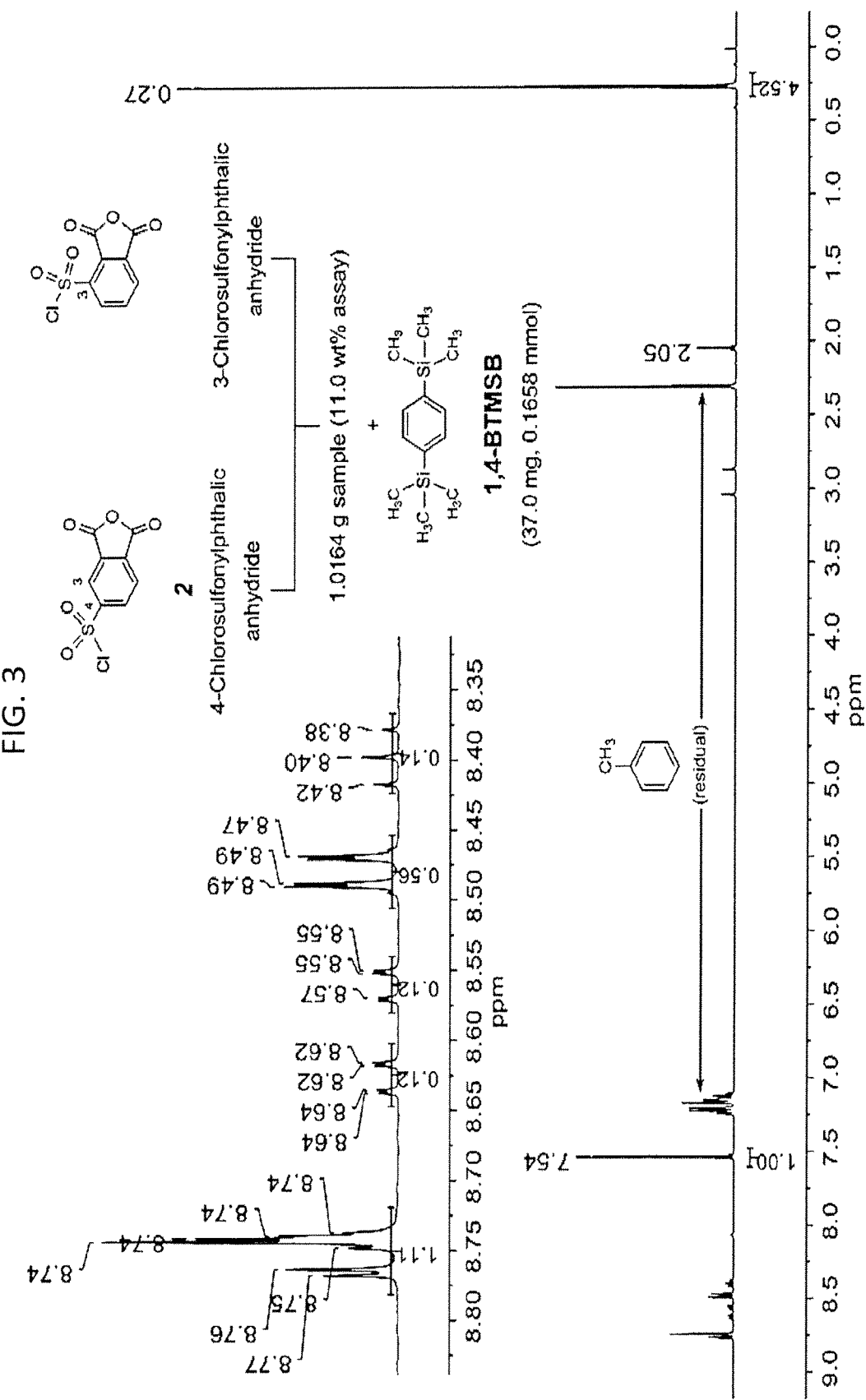
FIG. 3 is a $^1$H NMR spectrograph of 4-chlorosulfonylphthalic anhydride in accordance with an embodiment of the present disclosure.

$^1$H NMR spectrum (400 MHz, acetone-d$_6$) of isolated 4-chlorosulfonylphthalic anhydride (2, 4:1 mixture with 3-chlorosulfonylphthalic anhydride) with 1,4-BTMSB as an internal standard is shown in FIG. 3.

$^1$H NMR (400 MHz, acetone-d$_6$): δ 8.42 (dd, J=8.0, 8.0 Hz, 1H, 3-isomer), 8.51 (dd, J=1.0, 8.0 Hz, 1H, 4-isomer), 8.59 (dd, J=1.0, 8.0 Hz, 1H, 3-isomer), 8.64 (dd, J=1.0, 8.0 Hz, 1H, 3-isomer), 8.76 (dd, J=1.0, 2.0 Hz, 1H, 4-isomer), and 8.78 (dd, J=2.0, 8.0 Hz, 1H, 4-isomer).

4. Conversion of 4-Chlorosulfonylphthalic Anhydride (2) to 4-Azido-Sulfonylphthalic Anhydride (3)

This reaction is conducted in a jacketed 5-L, bottom drain glass reactor (150 mm diameter, ~2.5:1 depth/width ratio) that is equipped with an overhead stirrer motor, down-pumping two-tier 45° pitched 4-blade impeller (D=75 mm, 15 mm blade width, 75 mm tier separation), thermowell and thermocouple, nitrogen inlet, glass water condenser, and secondary bottom drain fitted with a threaded polytetrafluoroethylene (PTFE) plug. Temperature control is accomplished by recirculation of DowFrost (50:50 propylene glycol/water) heat transfer fluid through the reactor jacket. All liquid reagents are introduced through a dip tube that is fed with a PTFE diaphragm pump (Cole-Parmer model #7553-70) and Masterflex speed controller (Cole-Parmer model #7553-71). Beneath the 5-L reactor is a 3-L medium-porosity glass filter frit that drained into a 4-L plastic-coated glass Erlenmeyer filter flask. The filter flask is connected to a belt-drive vacuum pump and a dry ice (−78° C.) vacuum trap. A solution of 4-chlorosulfonyl phthalic anhydride (2) in toluene, (~5:1 mixture with 3-chlorosulfonyl-phthalic anhydride) (1270 g, 0.696 mol, 1.0 equiv, 14.1 wt % active) and fresh toluene (2215 g) are sequentially introduced into the 5-L reactor via the PTFE diaphragm pump. Agitation is initiated (150-200 RPM). The heat transfer fluid bath is turned on and the setpoint is adjusted to 20° C. A solution of sodium azide (90.6 g, 1.392 mol, 2.0 equiv) in deionized water (272 g) is prepared in a plastic-coated amber glass bottle and then the solution is added to the 5-L reactor via the PTFE diaphragm pump over a 7 min period. The bottle that contains the aqueous sodium azide is washed sequentially with deionized water (30 mL) and fresh toluene (30 mL). Both rinses are transferred to the 5-L reactor via the PTFE diaphragm pump. During the course of the aqueous sodium azide addition, the internal temperature of the reaction mixture increases from 19.5° C. to 22.3° C. Also, the appearance of a white insoluble (sodium chloride) is observed within ~30 seconds. After having been stirred for 1 h 18 min, a ~2 mL aliquot of the reactor slurry is removed.

The aliquot is passed through a 0.45 μm PTFE syringe filter and the filtrate is concentrated by rotary evaporation. Analysis of the residue by $^1$H NMR (acetone-d$_6$) reveals the starting material has been consumed. Once the NMR analysis is complete, the reaction mixture is drained through the reactor bottom drain and the salts are removed by vacuum filtration through a 3-L medium-porosity glass frit. The 5-L reactor and salt filter cake are washed with fresh toluene. The toluene filtrate is transferred in portions to a separatory funnel and the small amount of aqueous brine that remains is separated. The organic phase is washed with a minimal amount of deionized water and the aqueous phase is separated. The organic phase is partially concentrated by rotary evaporation to a mass of 1264.1 g.

Figure 4:
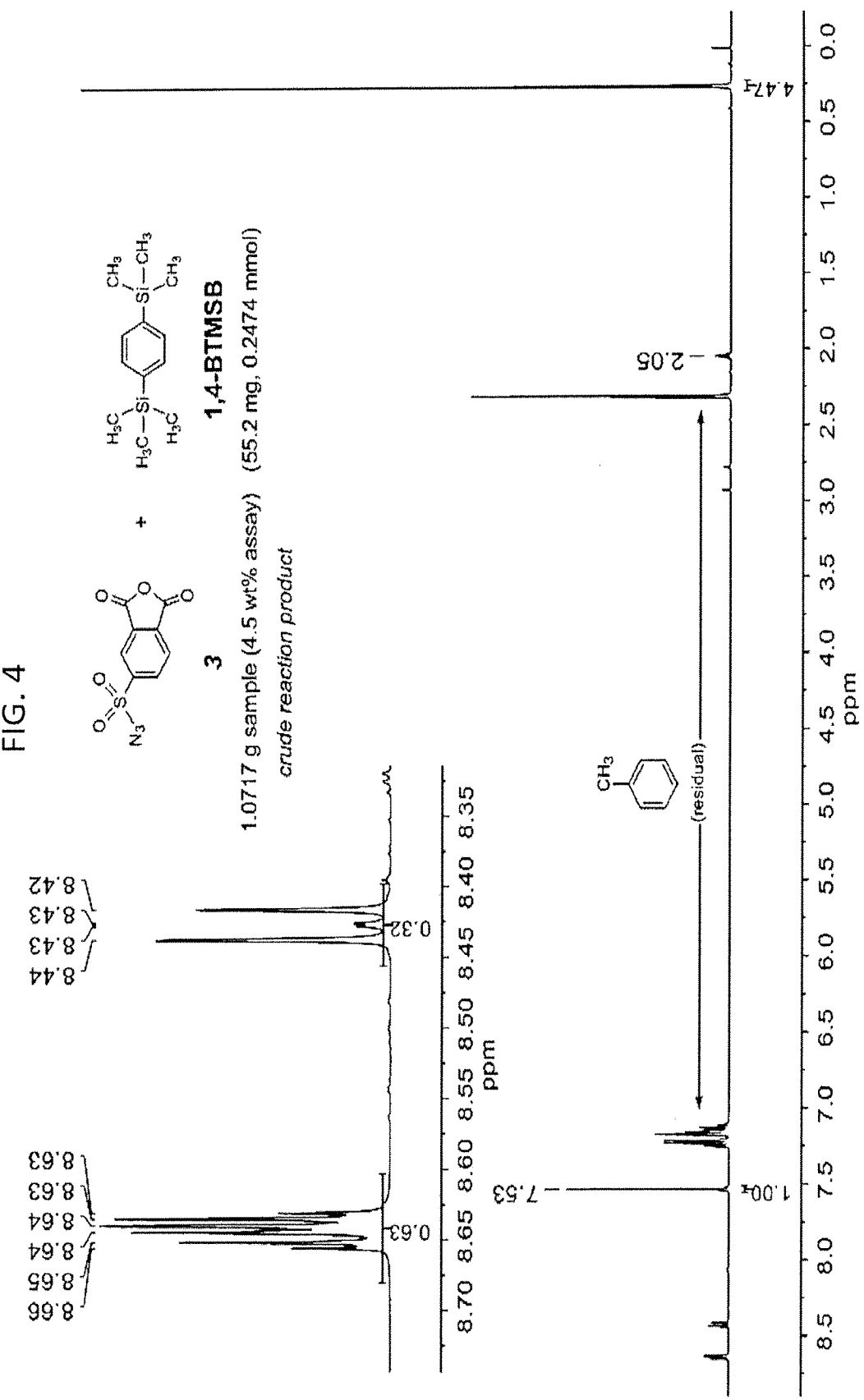
FIG. 4 is a $^1$H NMR spectrograph of 4-azidosulfonyl phthalic anhydride in accordance with an embodiment of the present disclosure.
Figure 5:
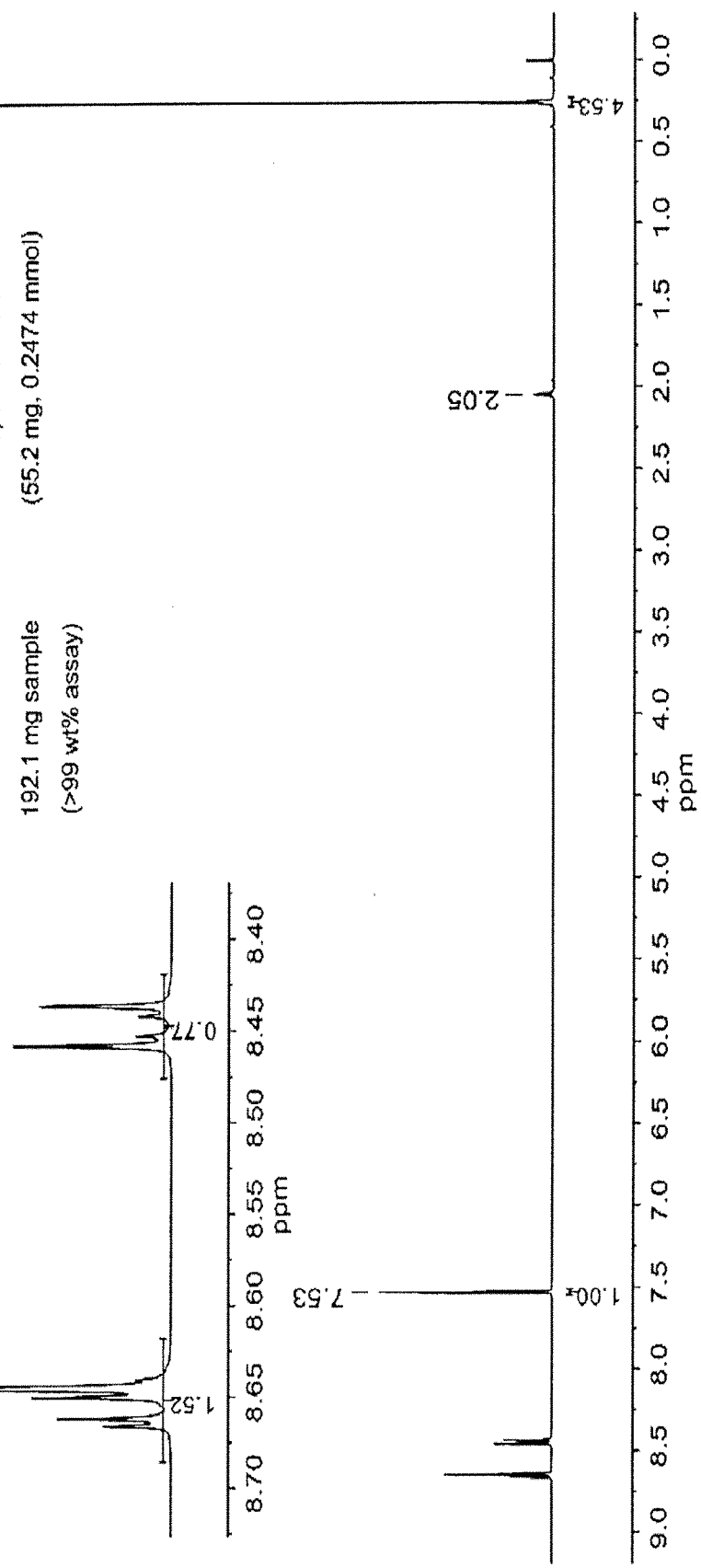
FIG. 5 is a $^1$H NMR spectrograph of 4-azidosulfonyl phthalic anhydride in accordance with an embodiment of the present disclosure.

A sample of this solution is removed (1.0717 g), evaporated to dryness, and combined with 1,4-BTMSB (33.3 mg, 0.1492 mmol). The resulting mixture is dissolved in acetone-d$_6$ (~4 mL). Analysis of this sample by $^1$H NMR indicates that the concentration of (3) is 4.5 wt %, which corresponds to an in-pot yield of 32%. FIG. 4 shows the $^1$H NMR Spectrum (400 MHz, acetone-d$_6$) of crude 4-azido-sulfonylphthalic (3) with 1,4-BTMSB as an internal standard. The toluene solution is further concentrated by rotary evaporation to leave behind a yellow solid (108.7 g). The crude solid is charged to a 1-L round-bottom flask fitted with a Teflon stir bar and a nitrogen inlet. Ethyl acetate (349 g) is added and the resulting mixture is stirred overnight. The homogenous yellow solution is treated with n-heptane (362 g), which induces the formation of cloudiness. The resulting mixture (838 g) is concentrated by rotary evaporation (25-30° C. @ ca. 50 mmHg) until ~⅔ of the total mass is taken overhead (279 g of slurry remained). The solids that form are recovered by vacuum filtration over a medium-porosity glass frit to yield 160 g of mother liquor. The wet cake is washed with 2:1 (v/v) n-heptane/ethyl acetate (2×150 mL) to yield 238.2 g of combined wash liquor. The wet cake (66.3 g) is dried in a vacuum oven at 40-50° C. to yield 4-azido-sulfonylphthalic anhydride (3) as a pale-yellow solid (51.2 g, 29% yield, 0.202 mol). A sample of (3) (192.1 mg) is combined with 1,4-BTMSB (55.2 mg, 0.2474 mmol) and the resulting mixture is dissolved in acetone-d$_6$ (~4 mL). Analysis of this sample by $^1$H NMR indicates that (3) is isolated in a state of high purity (>99 wt %). FIG. 5 shows the $^1$H NMR spectrum (400 MHz, acetone-d$_6$) of 4-azidosulfonyl-phthalic anhydride (3) with 1,4-BTMSB as an internal standard.

¹H NMR (400 MHz, acetone-d₆): δ 8.45 (dd, J=2.0, 7.0 Hz, 1H), 8.64 (dd, J=2.0, 2.0 Hz, 1H), and 8.65 (dd, J=2.0, 6.0 Hz, 1H).

¹³C NMR (100 MHz, acetone-d₆): δ 125.2, 128.0, 133.9, 135.7, 137.3, 146.1, 162.1, and 162.4.

Figure 6:
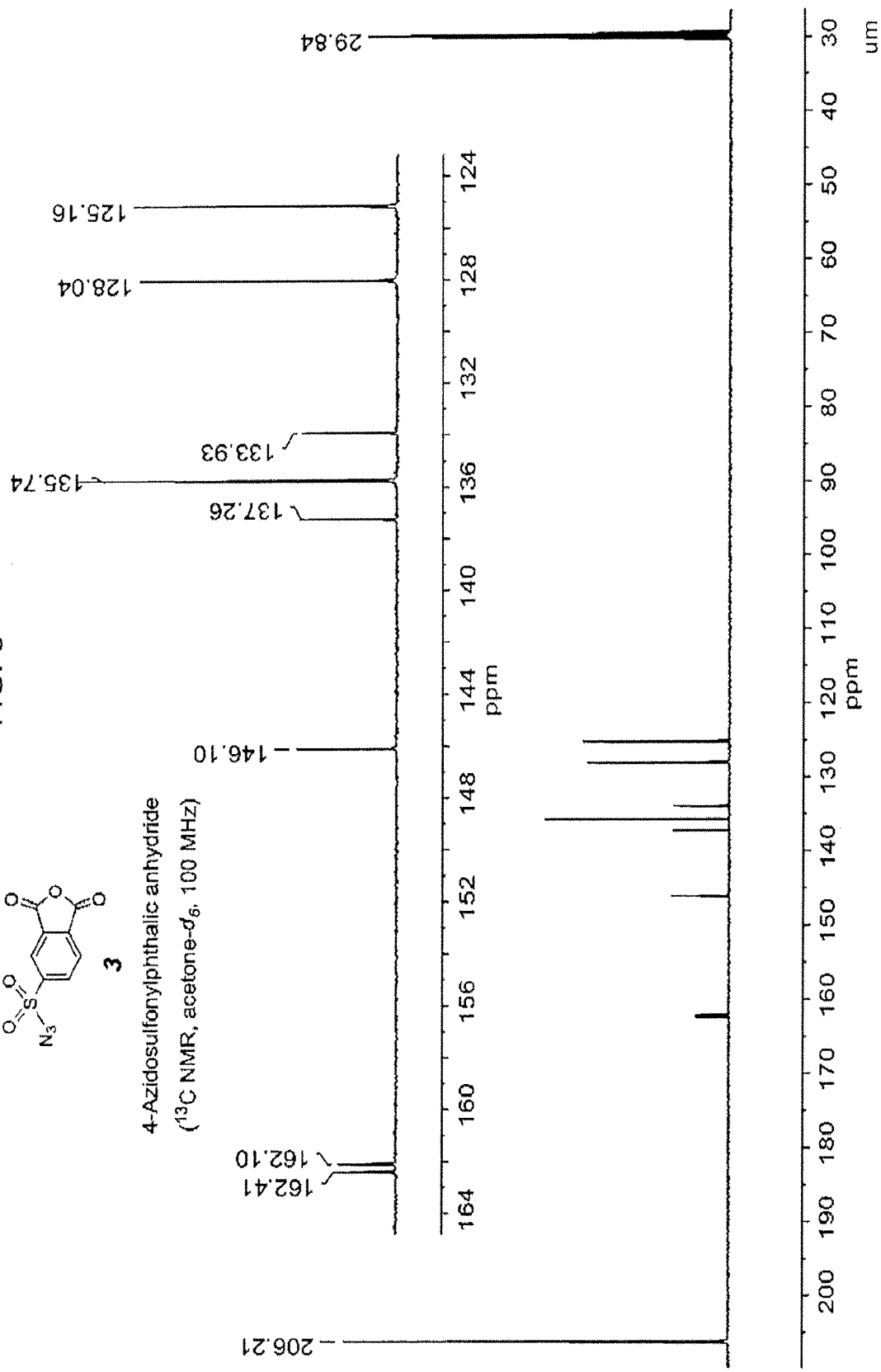
FIG. 6 is a $^{13}$C NMR spectrograph of 4-azidosulfonyl phthalic anhydride in accordance with an embodiment of the present disclosure.

FIG. 6 shows the ¹³C NMR spectrum of 4-azidosulfonylphthalic anhydride.

It is specifically intended that the present disclosure not be limited to the embodiments and illustrations contained herein, but include modified forms of those embodiments including portions of the embodiments and combinations of elements of different embodiments as come within the scope of the following claims.

We claim:

1. A process comprising:
chlorinating 4-sulfophthalic acid trisodium salt (1), under solvent reaction conditions, to form a dissolved 4-chlorosulfonylphthalic anhydride (2) and an insoluble sodium chloride;
first removing the insoluble sodium chloride from the dissolved 4-chlorosulfonylphthalic anhydride to form an isolated 4-chlorosulfonylphthalic anhydride;
reacting, under solvent reaction conditions, the isolated 4-chlorosulfonylphthalic anhydride with sodium azide to form a dissolved 4-azidosulfonylphthalic anhydride and an insoluble sodium chloride;
second removing the insoluble sodium chloride from the dissolved 4-azidosulfonylphthalic anhydride to form an isolated 4-azidosulfonylphthalic anhydride; and
retrieving a solid 4-azidosulfonylphthalic anhydride (3) from the isolated 4-azidosulfonylphthalic anhydride.

2. The process of claim 1 wherein the chlorinating comprises reacting the 4-sulfophthalic acid trisodium salt with a chlorinating agent in toluene solvent and in the presence of dimethylformamide.

3. The process of claim 1 wherein the first removing comprises filtering the insoluble sodium chloride from the dissolved 4-chlorosulfonyl anhydride.

4. The process of claim 2 wherein the dissolved 4-chlorosulfonylphthalic anhydride (2) in toluene solvent is a liquid non-aqueous phase, and the first removing comprises:
adding water to dissolve the insoluble sodium chloride in a liquid aqueous phase; and
separating the liquid aqueous phase from the liquid non-aqueous phase.

5. The process of claim 1 wherein the reacting step comprises adding the sodium azide directly to the isolated 4-chlorosulfonylphthalic anhydride.

6. The process of claim 1 comprising performing the process in a single reaction vessel.

7. The process of claim 6 wherein the chlorinating occurs in a solvent under solvent reaction conditions and the isolated 4-chlorosulfonylphthalic anhydride remains dissolved in the solvent.

8. The process of claim 7 wherein the reacting step occurs in the solvent under solvent reaction conditions and the isolated 4-azidosulfonylphthalic anhydride remains dissolved in the solvent.

9. The process of claim 8 wherein the reacting step comprises adding aqueous sodium azide to the isolated 4-chlorosulfonylphthalic anhydride in toluene solvent.

10. The process of claim 9 wherein the reacting step comprises adding aqueous sodium azide comprising from 5 wt % to 60 wt % sodium azide, based on the total weight of the aqueous sodium azide, to the isolated 4-chlorosulfonylphthalic anhydride in toluene solvent.

11. The process of claim 10 wherein the chlorinating comprises reacting the 4-sulfophthalic acid trisodium salt with a chlorinating agent comprising oxalyl chloride, in toluene solvent and in the presence of dimethylformamide.

12. A process comprising:
chlorinating 4-sulfophthalic acid trisodium salt (1), in toluene under solvent reaction conditions, to form a dissolved 4-chlorosulfonylphthalic anhydride (2) and an insoluble sodium chloride;
first removing the insoluble sodium chloride from the dissolved 4-chlorosulfonylphthalic anhydride to form an isolated 4-chlorosulfonylphthalic anhydride that remains dissolved in the toluene;
reacting, in toluene under solvent reaction conditions, the isolated 4-chlorosulfonylphthalic anhydride with aqueous sodium azide to form a dissolved 4-azidosulfonylphthalic anhydride and an insoluble sodium chloride;
second removing the insoluble sodium chloride from the dissolved 4-azidosulfonylphthalic anhydride to form an isolated 4-azidosulfonylphthalic anhydride that remains dissolved in the toluene;
retrieving a solid 4-azidosulfonylphthalic anhydride (3) from the isolated 4-azidosulfonylphthalic anhydride.

13. The process of claim 12 comprising performing the chlorinating, first removing, reacting, and second removing in a single reaction vessel.

14. The process of claim 13 wherein the chlorinating comprises reacting the 4-sulfophthalic acid trisodium salt with a chlorinating agent in toluene solvent.

15. The process of claim 14 wherein the reacting step comprises adding the aqueous sodium azide to the isolated 4-chlorosulfonylphthalic anhydride in toluene solvent.

16. The process of claim 15 wherein the dissolved 4-chlorosulfonylphthalic anhydride (2) in toluene solvent is a liquid non-aqueous phase, and the first removing comprises:
adding water to dissolve the insoluble sodium chloride in a liquid aqueous phase; and
separating the liquid aqueous phase from the liquid non-aqueous phase, wherein the 4-chlorosulfonylphthalic anhydride remains dissolved in the liquid nonaqueous phase.

17. The process of claim 16 wherein the chlorinating comprises reacting the 4-sulfophthalic acid trisodium salt with a chlorinating agent comprising oxalyl chloride, in toluene solvent and in the presence of dimethylformamide.

* * * * *